United States Patent
Van Den Honert et al.

(10) Patent No.: US 6,751,505 B1
(45) Date of Patent: Jun. 15, 2004

(54) METHOD AND APPARATUS FOR OPTIMIZING THE OPERATION OF A COCHLEAR IMPLANT PROSTHESIS

(75) Inventors: Chris Van Den Honert, Auroroa, CO (US); Ernst Ludwig Von Wallenberg, Muelheim (DE); Norbert Diller, Kusnacht (CH); Wai Kong Lai, Zurich (CH); Jochen Nicolai, Basel (CH); Mathias Stecker, Soelden (DE); Roland Laszig, Umkirch (DE); Joachim Mueller-Delle, Kiel (DE); Denise Cafarelli-Dees, Hants (GB)

(73) Assignee: Cochlear Limited, Lane Cove (AU)

( * ) Notice: Subject to any disclaimer, the term of this patent is extended or adjusted under 35 U.S.C. 154(b) by 0 days.

(21) Appl. No.: 09/936,455

(22) PCT Filed: Mar. 3, 2000

(86) PCT No.: PCT/AU00/00148

§ 371 (c)(1), (2), (4) Date: Apr. 30, 2002

(87) PCT Pub. No.: WO00/52963

PCT Pub. Date: Sep. 8, 2000

(30) Foreign Application Priority Data

Mar. 3, 1999 (AU) .............................................. PP8991
Aug. 27, 1999 (AU) .............................................. PQ2499

(51) Int. Cl.$^7$ .............................................. A61N 1/32
(52) U.S. Cl. .......................... 607/57; 607/62; 600/544; 600/559
(58) Field of Search .............................. 607/55, 56, 57, 607/62, 68; 600/544, 554, 559

(56) References Cited

U.S. PATENT DOCUMENTS

| | | | | |
|---|---|---|---|---|
| 4,612,934 A | * | 9/1986 | Borkan | 607/62 |
| 5,603,726 A | | 2/1997 | Schulman et al. | |
| 5,758,651 A | | 6/1998 | Nygard et al. | |
| 5,938,691 A | | 8/1999 | Schulman et al. | |
| 6,205,360 B1 | * | 3/2001 | Carter et al. | 607/57 |

FOREIGN PATENT DOCUMENTS

| | | |
|---|---|---|
| WO | WO 94/14376 | 7/1994 |
| WO | WO 97/09863 | 3/1997 |
| WO | WO 97/48447 | 12/1997 |
| WO | WO 99/66982 | 12/1999 |

OTHER PUBLICATIONS

Abbas et al., "Summary of Results Using the Nucleus C124M Implant to Record the Electrically Evoked Compound Action Potential," Ear & Hearing 1999;20;pp. 45–59.*

* cited by examiner

Primary Examiner—Kennedy Schaetzle
(74) Attorney, Agent, or Firm—Gottlieb, Rackman & Reisman, P.C.

(57) ABSTRACT

Disclosed is a method and apparatus for controlling the operation of a Cochlear implant prosthesis to optimise the effect of stimulation for a given patient. The optimal operation mode is determined in accordance with predetermined parameters measured from the neural response of the patient's auditory system in response to a neural stimulation.

15 Claims, 3 Drawing Sheets

METHOD AND APPARATUS FOR OPTIMIZING THE OPERATION OF A COCHLEAR IMPLANT PROSTHESIS

FIELD OF THE INVENTION

The present invention relates to cochlear implant prostheses and in particular to a method and apparatus for adjusting the operation of such a prosthesis in order to optimise the benefit of the therapy provided by the prosthesis to a user.

BACKGROUND

It is known that individual patients using a cochlear implant system differ in their ability to benefit from different speech coding strategies. These coding strategies may differ in the number of channels activated, the dynamic or fixed allocation of channels to electrodes and the rate of stimulation for each channel. For example, some patients show significant improvements in open-set speech understanding when converting from a relatively low rate of stimulation of 250 Hz per channel (for example as provided by the SPEAK stimulation strategy used in some of the products manufactured by the applicant) to rates of 1200 Hz per channel or more (for example as provided by the ACE stimulation strategy also used in some of the products manufactured by the applicant) while other stimulation parameters, such as the number of channels and their allocation to electrodes remain unchanged. Other patients show no improvement, or even a reduction in benefit, when the stimulation rate is increased from low rates to high rates.

Consequently at present the adjustment of operation of the implant in order to optimise the benefit of the therapy provided to a patient by a cochlear implant prosthesis is to some extent a hit-or-miss affair. In particular comments must be sought from the patient as to whether or not the benefit of the prosthesis is improved or decreased upon making an adjustment in operation. There are a number of problems associated with this prior art approach. For example the adjustment is not made according to any quantitative parameter but rather is based on the somewhat subjective judgements of the patient.

Furthermore some patients, for example young children, may not be able to readily indicate an improvement or decrease in the quality of their hearing perception during the adjustment process. Yet a further problem is that the present approach does not readily lend itself to automation, relying as it does on the conscious feedback of the patient.

It is an object of the present invention to provide a method for setting a cochlear implant prosthesis to an appropriate operation mode which overcomes the previously described problems.

SUMMARY OF THE INVENTION

According to a first aspect of the invention, there is provided a method for adjusting the operation of a cochlear implant prosthesis, said method including the steps of:
   recording at least one neural response in respect of at least one electrode of said cochlear implant prosthesis;
   b) determining a selected parameter from said recording;
   c) determining an optimum operation mode for said cochlear implant prothesis selected on the basis of said selected parameter; and
   d) adjusting the operation of said cochlear implant prosthesis to operatively cause said cochlear implant prosthesis to operative in said optimum operation mode.

According to a second aspect a method for adjusting the operation of a cochlear prosthesis including the steps of:
   a) recording neural responses in relation to a plurality of electrodes of said cochlear implant prosthesis;
   b) determining a corresponding plurality of selected parameters from said neural responses;
   c) calculating a combined selected parameter from at least some of said plurality of selected parameters;
   d) determining an optimum stimulation rate on the basis of said combined selected parameters; and
   e) adjusting the operation of said cochlear implant prosthesis thereby causing said prosthesis to operatively apply stimulations to at least some of said plurality of electrodes, all of said plurality of electrodes, and/or any other available electrodes, at a rate dependent on said optimum stimulation rate.

According to third aspect a system for adjusting the operation of a cochlear prosthesis, said cochlear prosthesis including a means for evoking neural responses of the auditory system to applied stimulation, said system including:
   a) processing means coupled to said cochlear prosthesis and arranged to analyse said neural responses in order to determine an optimal performance mode dependent on at least one selected parameter derived from said neural responses and to cause said cochlear prosthesis to operate in said optimal mode;

DETAILED DESCRIPTION

Neural Response Telemetry (NRT) is well known in the art. For example an NRT system in the context of a cochlear prosthesis is described in U.S. Pat. No. 5,758,651, assigned to the present applicant and hereby incorporated by reference. It has been found that various neural response measurements carry a wealth of information about the behaviour of the auditory nerve fibres in response to electrical stimulation. As such, many different forms of measurement may be made, which in turn may lead to adjustment of varying operating parameters of an auditory prosthesis according to the needs and capacities of an individual user.

Figure 1A:
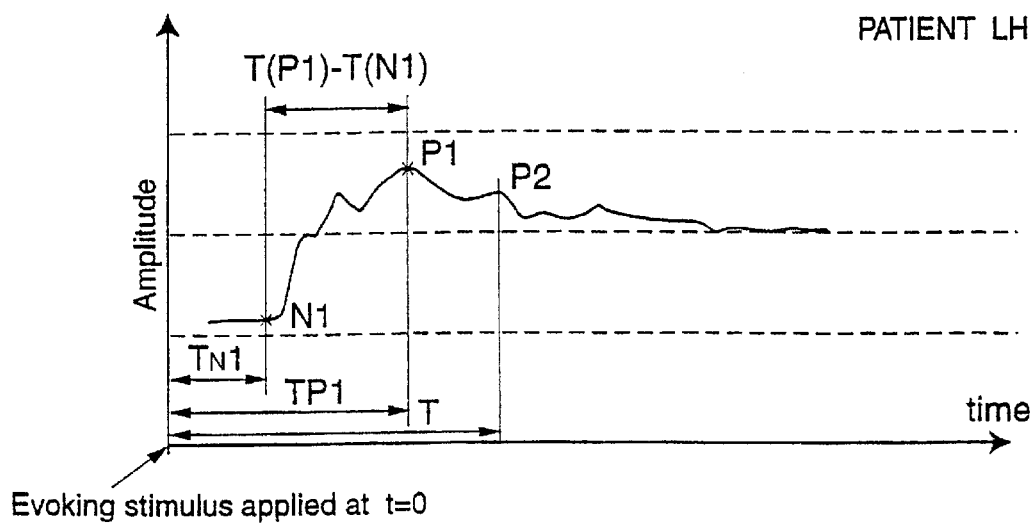
FIG. 1A illustrates a neural response waveform recorded in respect of a first patient.
Figure 1B:
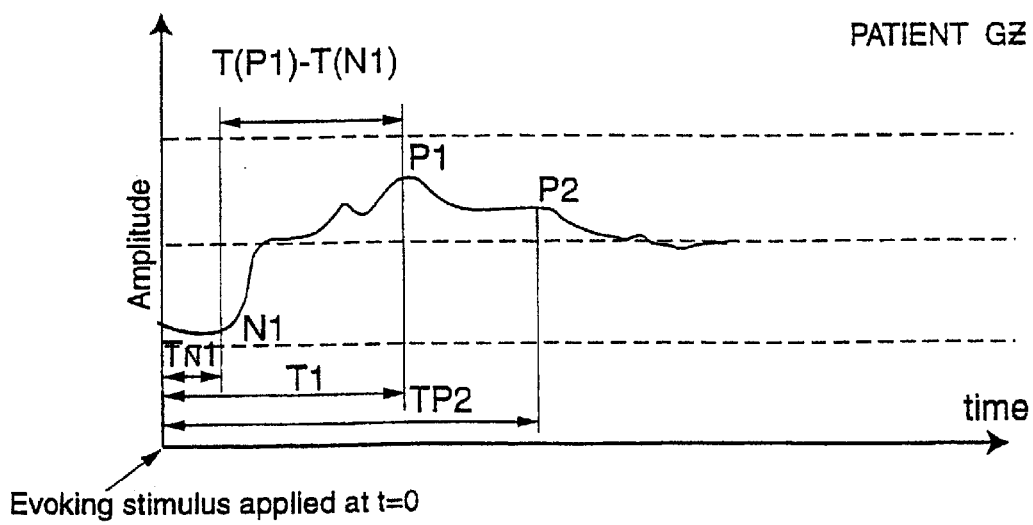
FIG. 1B is a graph of a neural response waveform recorded in respect of a second patient.

In the context of this application and as can be seen in FIGS. 1A and 1B, a neural response whose properties are to be measured comprises an electrical potential which varies with time (producing a "Wave form") and is generated by activity within the fibres of the auditory nerve or cochlear nucleus. Most commonly, an individual wave form comprises a peak of negative potential (usually termed N1), sometimes followed by a peak of positive potential (usually termed P1), followed by a return to baseline (approximately zero potential). In some cases, a peak of positive potential (P2) may precede the N1 peak. However, the wave form morphology may differ due to variations in recording electrode geometry or position, underlying neural synchrony, or pathological condition of the nerve fibres. Individual wave forms are often characterised by "magnitude" which refers to the potential difference between some feature of the wave form (for example N1 peak) and another (for example the P1 peak or the baseline). Such magnitudes depend upon a number of conditions such as the number of fibres activated, their synchrony, the strengths of the individual fibre activities, and the geometric relationships among the fibres and the recording electrodes (including distances and angles).

Such wave forms can be measured from electrodes positioned within or near the cochlea. An electrode of an apparatus for measuring such potentials is disclosed in previously referenced U.S. Pat. No. 5,758,651. However other apparatus, not necessarily incorporated within the prosthesis itself, may also be used to perform such a measurement.

Generally, measurement of the neural response involves:
a) delivery of an electrical stimulus current through a set of two or more electrodes which current activates some or all fibres of the auditory nerve, and
b) subsequent recording of the ensuing electrical potential signals generated by the activated fibres. The recording may be performed using the same electrodes which carried the stimulus, or different electrodes. The electrodes used to perform the recording must be within or in the immediate vicinity of the cochlea (ie not on the scalp).

In its simplest form, the measurement is performed using a single excitatory current pulse (for example a biphasic current pulse) as a stimulus, followed by a measurement of a single potential wave form which constitutes the neural response. More generally, the stimulus may comprise a complex sequence of electrical current wave forms and the response may similarly comprise a sequence of potential wave forms generated by the fibres of the auditory nerve. An example of a slightly more complex sequence is the presentation of two equal-intensity stimulus current pulses in rapid succession, and the recording of two potential wave forms, one in response to each pulse. A still more complex stimulus may comprise a sequence of multiple current pulses of varying intensity. In this case, the neural response may be a similar sequence of potential wave forms, each following one of the pulses, or alternatively each associated with some feature of the stimulus such as a maximum in its intensity envelope.

For simplicity, the use of the term "pulse" will refer to a component of a stimulus. However, it should be clear that the term "pulse" is not restricted to any particular wave shape such as a biphasic rectangular pulse. It refers more generally to any momentary variation in current which constitutes a subcomponent of an overall stimulus. A stimulus may comprise a single "pulse" or a long and complex sequence of many "pulses".

The entire stimulus may be delivered through a single set of electrodes, or different pulses may be delivered through different sets of electrodes. For example, a sequence of three pulses may be delivered through a single pair of electrodes, or alternatively, a different pair of electrodes may be selected for delivery of each pulse of the stimulus. Similarly, the entire response may be measured from a single set of electrodes, or a sequence of potentials measured using different recording electrodes for each potential. Some or all of the electrodes used for delivery of the stimulus may also be used for recording the response, and some or all of the electrodes may be used to deliver the stimulus. Alternatively, the electrode sets used for stimulation and recording may be completely separate.

The particular stimulus to be employed is determined by the response property of interest as would be understood by one skilled in the art.

Regardless of the particular stimulus employed, signal averaging may be used to improve the clarity of the recorded potential wave forms (responses). This process involves repeating the entire stimulus and recording process two or more times using the identical stimulus each time, and then averaging the two or more resulting responses together. Such averaging serves to reduce the noise in the response and is a well known method.

The response properties of interest will include neural response properties, which could fall into three possible categories. For example, these categories could be temporal properties, spatial properties and spatio-temporal properties.

Temporal properties of the neural response depend upon timing between various features of the stimulus or various features of the response wave forms, or both. Often, these properties are also characterised by response wave form magnitude and its dependence on such timing, or on stimulus intensity, or both. Examples of temporal properties and relationships which may be used to quantify each of these properties include:

1. Latency—latency is the time delay from onset or offset of a stimulus (or other feature of the stimulus such as a envelope maximum) to the occurrence of a particular response feature such as the N1 peak or P1 peak.

This property can be quantified by a relationship such as Latency (L)=tz $-t_1$, where $t_1$ is the time at which a stimulus begins, and tz is the time at which the $N_1$ peak of the response occurs.

2. Integration—integration refers to the effective summation of two or more stimulating pulses occurring in rapid succession which, acting in concert, achieve more effective stimulation than if each were presented alone. For example, a sequence of two or more pulses presented in rapid succession may generate a response wave form with a greater magnitude than would be generated by either individual pulse alone. Integration may be characterised by the measured relationship between inter-pulse interval and wave form magnitude. Alternatively, it may be characterised by the measured relationship between inter-pulse interval and stimulus intensity required to achieve a specified response wave form magnitude. Many other parametric relationships may also readily defined to characterise integration.

One possible way of quantifying the property of integration is to consider that it can be characterised by parameter U in the equation:

$$Q(t)=Mo(1+e^{-t/u})$$

Where U is determined by a curve fitting procedure which minimises the error between the function Q(t) and a sequence of n parameters $Q_1, Q_2, \ldots Q_n$ determined for a sequence of n delay values $t_1, t_2, \ldots t_n$. In each case, $$Qi+Mi/Mo$$

Where Mo is the magnitude of a response elicited by a single stimulus presented in isolation, and Mi is the magnitude of a response elicited by two identical stimuli presented in rapid succession separated by delay $t_1$.

3. Refractoriness—refractoriness refers to the inability of a nerve fibre to discharge multiple times in rapid succession. If two or more stimulus events are presented in rapid succession, the corresponding sequence of response wave forms may exhibit decrements or fluctuations in magnitude among successive wave forms, or in some cases a complete absence of some responses. Refractoriness may be characterised by the relationship between inter-pulse interval and stimulus intensity threshold for eliciting a second, third or nth response. Alternatively, it may be characterised by the relationship between inter-pulse interval and the decrement in magnitude (or latency) between successive response wave forms. Many other parametric relationships may also be readily defined to characterise refractoriness.

One possible way of quantifying the property of refractoriness is to consider that it can be characterised by the parameter W in the equation:

$$M(t)=Mo(1-e^{-((t+a)/W)})$$

where 'a' and 'W' are determined by a curve fitting procedure which minimises the error between the function M (t) and a sequence of 'n' response magnitudes $M_1, M_2, \ldots M_n$. Those magnitudes are determined by presenting 'n' pairs of identical stimuli, with delays $t_1, t_2, \ldots t_n$ between the two stimuli of each pair. Each magnitude Mi is the magnitude of the second response elicited from a given pair, and Mo is the magnitude of the first response (which does not vary the delay).

4. Stimulus following—generally, when the intensity of a single stimulus pulse is increased (between the limits of response threshold and response saturation) the magnitude of the corresponding response wave form increases. However, due to complex interactions of refraction and integration, when multiple stimulating pulses occur in rapid succession and with varying intensity, the correspondence between pulse intensity and response magnitude may not be preserved. As a result, the extent to which the envelope of response magnitudes follows the envelope of pulse intensities may vary with the inter-pulse interval (or equivalently, pulse rate). Stimulus following may be characterised by the measured relationship between inter-pulse interval and ratio of stimulus intensity modulation depth to response wave form magnitude modulation depth. An alternative measure of stimulus following has been described by Wilson et al Research Triangle Institute NIH Contract No. 1-DC-5-2103 Quarterly Progress Report 7: February 1 through Apr. 30, 1997. Those investigators described waxing and waning of response magnitudes in response to successive equal intensity pulses. The magnitude of the alteration and its relationship to inter-pulse interval has been used to characterise stimulus following. Stimulus following may be also characterised using a series of pulses in which only one pulse differs in intensity from the others, which produces a singularly larger or smaller response magnitude. Many other parametric relationships may also readily defined to characterise Stimulus Following.

One possible way of quantifying the property of Stimulus Following is to consider that it can be characterised by the relationship:

F=$D_2/D_1$ where $D_1$ is the depth-of-modulation of an aptitude modulated pulse train, and $D_2$ is the depth-of-modulation of train of elicited responses. Depth-of-modulation is defined as follows:

D1=$1-(I_{min}/I_{max})$ where $I_{max}$ is the intensity of the strongest pulse in the train, and $I_{min}$ is the intensity of the weakest pulse.

D2=$1-(M_{min}/M_{max})$ where $M_{max}$ is the magnitude of the largest response, and $M_{min}$ is the magnitude of the smallest response.

With regard to the second considered category of neural response properties, spatial properties of the neural response are determined from spatial distances between stimulating and/or recording electrodes. Often, these properties are also characterised by response wave form magnitude and its dependence on such distances, or on stimulus intensity, or both. For a given set of conditions (for example electrode sets, pulse width, pulse rate) the relationship between stimulus intensity and corresponding measured response magnitude is referred to as input-output or I/O function. Examples of spatial properties and possible relationships which may be used to quantify each of these properties include:

Spread of Excitation—Spread of Excitation refers to the extent to which a stimulus which is delivered at a single site within the cochlea excites nerve fibres not only near the site, but also at various distances from the site. When the stimulus is delivered at a single site (through a fixed electrode set), recordings of the response may be made through various electrode sets at different distances from the stimulating electrode set (either simultaneously, or sequentially by repeating the stimulus). Spread of Excitation may be characterised by the relationship between response magnitude and distance of the recording site from the stimulating site. The process may be repeated for many stimulus intensities such that a full I/O function is measured at each recording site. In this case, Spread of Excitation may be characterised individually at each intensity or by the relationship between some feature of I/O curve (for example threshold or midpoint or slope) and distance. Similarly, Spread of Excitation may be measured by fixing the position of the recording site, and presenting stimulation through electrodes at various distances from the recording site. Many other parametric relationships may be also readily defined to characterise Spread of Excitation.

One possible way of quantifying the property of Spread of Excitation is to consider that it can be characterised by the parameter Z in the equation M (x)=$Ae-x/Z$ where A and Z are determined by a curve fitting procedure which minimises the error between function Mx and a sequency of n response magnitudes $M_1, M_2, \ldots M_n$ measured at n recording sites located at distances $x_1, x_2, \ldots x_n$ from the Stimulus Site. Parameter Z is sometimes referred to as a "space constant".

Overlap of Stimulation—given that stimulation may spread to varying distances from the stimulating electrodes (depending on stimulus intensity and electrode geometry), some nerve fibres may fall within regions where they are subject to simulation by currents from multiple stimulating electrodes sets. Thus, when stimuli are simultaneously delivered by two or more sets, those nerve fibres may experience complex combinations of stimuli which have additive or cancelling effects on the net excitation. The existence of such regions of overlap often referred to as "channel interaction". It limits the independence of stimuli delivered through separate electrode sets which are to be intended to act discretely upon isolated groups of nerve fibres. Overlap of stimulation may be characterised by the relationship between response magnitude, intensities and polarities of stimulation through two or more electrode sets, and the distances among the stimulating electrode set. Many other parametric relationships may also be readily defined to characterise overlap of stimulation.

One possible way of quantifying the property of Overlap of Stimulation is to consider that it can be characterised by O=$(I_2-I_1)/I_1$, where $I_1$ is the threshold intensity required to elicit a response to a first stimulus delivered through a first electrode set when the first stimulus is presented alone, and $I_2$ is the threshold intensity for a stimulus delivered through the first electrode set when a second stimulus is delivered concurrently through a second electrode set.

Density of Innervation—density of innervation refers to the number of surviving nerve fibres (or cell bodies) per unit of volume or distance at any particular point in the cochlea. Many etiologies of deafness result in non-uniform neural survival, such that the density of innervation is "patchy" or inconsistent at various intervals within the cochlea. The magnitude of the response depends upon in part on the number of activated nerve fibres so it can be used to infer an estimate of local innervation density. By comparing response magnitudes with stimuli delivered at various sites, or recordings at various sites, or both, local innervation density may be estimated. Density of innervation may be characterised by the relationship between response magnitude and recording site (or stimulating sites, or both). Similarly, density of innervation may be characterised by the relationship between a particular feature of the I/O function (for example threshold, slope) and the recording site (or stimulating site, or both).

One possible way of quantifying the property of Density of Innervation is to consider that it can be characterised by S in the following equation:

$$M(I)=SI+\rho$$

where S and $\rho$ are determined by a linear regression through a sequence of n response magnitudes $M_1$, $M_2$, ... $M_n$ measured at n corresponding stimulus intensities $I_1, I_2, \ldots I_n$.

As discussed above, the third category of neural response properties is spatial-temporal properties. Spatial-temporal properties include those properties of the neural response which vary with both timing (as described with reference to temporal properties above) and the selection of stimulation or recording electrode sites (as described with reference with spatial properties). As such, they comprise the combination of 1. temporal properties described above in the circumstance where the presumption of fixed stimulus and recording site is removed and
2. spatial properties described above in which the presumption of simultaneous stimulation at two or more sites is removed.

Masking—masking refers to the influence of a second (masking) stimulus on the response which is otherwise elicited by a first (probe) stimulus. For brevity, we use the term masking to describe either a decrement in the response of the probe (traditional usage) or increment in the response to the probe (sometimes described as "facilitation"). The influence of interest may be either a modification of the response magnitude or the response latency.

When both masker and probe are delivered through a single set of stimulating electrodes at different moments in time, this is a manifestation of refractoriness or integration as described above. Also, when both masker and probe are delivered simultaneously through different electrode sets, this relates to overlap of stimulation which is also described above. However, it is also possible to deliver (two or more) stimuli non-simultaneously to different electrode sets. The resulting influence of the masker on the response to the probe represents a measure of spatial-temporal interaction. Masking can be characterised by the multi dimensional dependence of magnitude (or latency) of the probe response upon:

a) the distance between stimulating electrode sets;
b) the separation in time of the masker and probe;
c) intensity of the masker;
d) the intensity of the probe; and
e) the distances between the recording electrodes and the stimulating electrode sets.

Masking can be extended to incorporate stimuli by two or more electrode sets, each receiving different stimuli, with arbitrary timing relationships among maskers and probe. In addition, the masker stimulus can be a single pulse, or arbitrary complex train of pulses. In its generalised form, masking subsumes the properties of refractoriness and integration when either is characterised using more than a single set of stimulating electrodes.

One possible way of quantifying the property of Masking is to consider that it can be characterised by the following equation:

$$M=(I_2-I_1)/I_1$$

where $I_2$ and $I_1$ are as defined above for Overlap of Stimulation. In this case, the first and second stimuli are separated in time by a specified delay.

Interleaving—trains of stimuli which are presented non-simultaneously to two or more sets of stimulating electrodes are often described as "interleaved". Stimulus Following as described above may be characterised using such interleaved stimuli with responses recorded at one or more sites. The metric of Stimulus Following may vary with distances among electrodes as well as repetition rate and recording location.

As outlined above, a large set of response properties can be measured, each of which gives insight into the capacities of the individual's auditory periphery. The decision about which parameters to optimise from which properties may vary from individual to individual. However, the process by which such properties guide parameter selection can be described.

Strategy Selection

Speech processing strategies are distinguished in part by the manner in which speech signals are encoded. For example, CIS (Continuous Interleaved Sampling) uses pulses at relatively high rates delivered through relatively few widely spaced electrodes to represent speech, whereas SPEAK uses relatively low rates and a relatively large number of closely spaced electrodes.

Therefore, SPEAK would be preferred over CIS if response properties show evidence of poor neural behaviour at high pulse rates (for example such as slow recovery from refractoriness, long integration time, poor stimulus following at high rates). Conversely, CIS would be preferred if response properties show evidence of poor spacial selectivity (broad spread of stimulus, large overlap of stimulation). Similarly, any strategy which is vulnerable to channel interaction (SAS-Simultaneous Analogue Stimulations) should be avoided if there is substantial overlap of stimulus. Therefore, by measuring neural response properties, the most optimal speech processing strategy can be selected to provide the most benefit to the individual.

The following examples illustrate relationships which may be used to optimise strategy selection based on measured neural response properties. It should be appreciated that these relationships are exemplary only and other similar optimising relationships may be further defined which still fall within the scope of the present invention.

1. A high rate strategy (CIS or ACE) may be selected if the mean refractoriness value W computed for two or more electrodes falls below a threshold value $W_{max}$. Otherwise, a low rate strategy (SPEAK) may be selected.

2. A strategy utilising many electrodes (SPEAK, ACE) may be selected if the mean overlap measure $O_{avg}$ falls below a threshold value $O_{max}$. Otherwise a strategy utilising fewer electrodes (for example CIS) may be selected.

3. A composite parameter which includes weighted contributions from measures of overlap, refractoriness, Stimulus Following and Spread of Excitation may be defined:

C=aO+bW+cF+dS, where a,b,c and d are predetermined constants. Such a composite parameter may be used in place of individual parameters and compared against similarly defined predetermined threshold values.

Parametric Optimisation

Within the parametric space of a given strategy, individual parameters may be optimised based on neural response properties. The ACE strategy provides many options for rate and number of electrodes. Measures of spatial-temporal interaction (for example masking) can identify the optimum trade off between rate and channel-spacing to avoid exceeding the temporal capacity of nerves. In general, for pulse style strategies, Refractoriness, Integration and Stimulus Following measures can identify the highest rate which can be employed without exceeding peripheral capacity. Innervation density can be used to identify electrodes which should be excluded from the MAP due to lack of proximate target neurons. Spatial-temporal measures such as masking can determine the optimum electrode sequence order (stagger order) to minimise channel interactions with sequential pulse strategies. In cases where the number of available number of electrodes exceeds the number required for a particular strategy, temporal response properties can identify the optimal subset of electrodes which will be effective with high rate stimulation, while spatial properties can identify electrodes to be avoided due to excessive stimulus overlap.

The following examples illustrate relationships which may be used for electrode selection and parametric optimisation based on measure neural response properties. It should be appreciated that these relationships are exemplary only and other similar optimising relationships may be further defined which still fall within the scope of the present invention.

Electrode Selection:

1. An electrode may be excluded from a patient map if the corresponding measure of innovation density S falls below a threshold value $S_{min}$.

2. An electrode may be excluded from a high-rate map if it exhibits poor ability to follow a high-rate stimuli as evidenced by:

Refractoriness W which exceeds a threshold value $W_{max}$

Stimulus Following which falls below a threshold value $F_{min}$ for a predetermined pulse rate.

3. Electrode may be excluded from a map if they exhibit overlapping stimulation which exceeds a threshold value $O_{max}$ at a predetermined stimulus intensity I.

Parametric Optimisation:

1. Stagger order (the sequence with which electrodes are selected for stimulation). May be optimised by selecting a sequence which minimises the sum of stimulus overlap measures O or masking measures M across successive sites in the sequence.

2. Stimulus rate may be optimised by determining the highest rate for which the mean measure of refraction $W_{avg}$ falls below a threshold value $W_{max}$. Alternatively, stimulus rates may be determined individually for each electrode by comparing the individual measure W for each electrode against a similar threshold.

3. When stimulus rates and number of electrodes to be used are subject to a combined limit (for example, an aggregate rate imposed by the prosthesis), the trade-off between rates and number of electrodes may be optimised by selecting from among available rate/electrode combinations that combination which minimises the mean masking measure M.

4. The intensity of a conditioning stimulus may be determined from the minimum intensity which yields a Stimulus Following measure F which exceeds a predetermined threshold value $F_{min}$.

5. The rates of a conditioning stimulus may be determined by selecting the rate which maximises the Stimulus Following measure F.

Conditioner Tuning

Recently, it has been proposed that additional currents be exploited in addition to those introduced to represent the sound stimulus itself. These additional currents are described as "conditioners" whose purpose is to introduce stochastic variability in the neural discharges, more closely mimicking the natural hearing process. Conditioners are generally envisioned to take the form of high rate pulse trains or analogue noise current. Stimulus following has been proposed as metric of merit for assessing the effect of conditioners. Therefore, measurement of stimulus following may be used to determine the optimum intensity, rate, spectral content or spatial distribution of conditioning stimuli for an individual.

The remaining discussion will provide a more detailed description of one particular application of the present invention, namely the optimisation of stimulation rate in response to various parameters derived from neural response as described above.

According to one embodiment of the present invention a subject implanted with a cochlear implant prosthesis incorporating an NRT system is stimulated to evoke at least one neural response measured in respect of at least one electrode.

Referring now to FIGS. 1A and 1B there are shown neural responses each made from a different patient for an electrode located at approximately the same position relative to the patient's cochlea. It will be noted that the shape of the waveform that has been elicited differs from patient to patient.

Neural response waveforms include typical identifiable features. For example, N1 denotes the first negative peak of the neural response. P1 denotes the first positive peak of the neural response while P2 denotes the second positive peak.

The present method is based on the inventors' discovery that the various parameters associated with a neural response waveform may be used to predict those patients which will benefit from a high-rate stimulation strategy, for example a strategy applying stimulations at 1200 Hz and above (such as the aforementioned ACE strategy), as compared with those who do not so benefit but are better suited to a low rate strategy, for example one applying stimulations at 250 Hz (such as the previously referred to SPEAK strategy).

A preferred parameter for use in determining a desired stimulation rate is a latency associated with a given neural response waveform. However, other parameters, such as EP amplitude, I/O function parameters (e.g. threshold or slope) and refraction curve properties may be used to determine appropriate stimulation rates. As has been previously described, it will be understood that appropriate relationships between these parameters and the desired stimulation rate may be determined empirically as is well within the skill of the person skilled in the art.

The time period between the occurrence of P1 and N1 is one such latency. Another is the time period between the application of stimulation and the occurrence of N1, P1, or P2. Other latency periods may also be calculated with reference to other identifiable waveform features. In particular the inventors have discovered that the longer the latency period the lower the rate of stimulation indicated to be appropriate, whereas if the latency period is shorter then the use of a higher rate stimulation is indicated in order to improve the benefit of the therapy conferred by the cochlear prosthesis.

Referring again to FIG. 1 it will be noted that patient LH exhibits a T(P1)–T(N1) latency of 200–300 μs whereas patient GZ exhibits a T(P1)–T(N1) latency of 400–500 μs. Using the latency value as an argument in a mathematical function, an optimised stimulation rate can be determined. Several mathematical functions R=f(Δ) are available where R is the optimised rate and Δ is a latency period derived from the neural response waveform. For example one very simple model is: If Δ<K then R=A, else R=B where A>B and K is a constant. Such a model is used where two stimulation rates, A and B, are available and K is a predetermined constant. Another model might be that R=(c1/Δ)+c2 where c1 and c2 are constants.

The constants K, c1, c2 of the above models are derived by reference to patients whose optimal stimulation rates have been found by means of prior art methods. For example, for the first method where Δ is the time between the occurrence of N1 and P1, A=250 Hz and B=1200 Hz then a value of K=350 μs has been found to be suitable. For the second method the values c1=2850 Hz and c2=225 μs have been suitable where, once again, the latency period has been measured between N1 and P1. It will be understood by the person skilled in the art that these functions are only illustrative of the type of relationships that may be suitable and that many other functions may be equally defined to establish the relationship.

For example, one method of defining a suitable function is by examination of latency-to-optimal-rate relationships measured empirically with another optimisation means.

Figure 2:
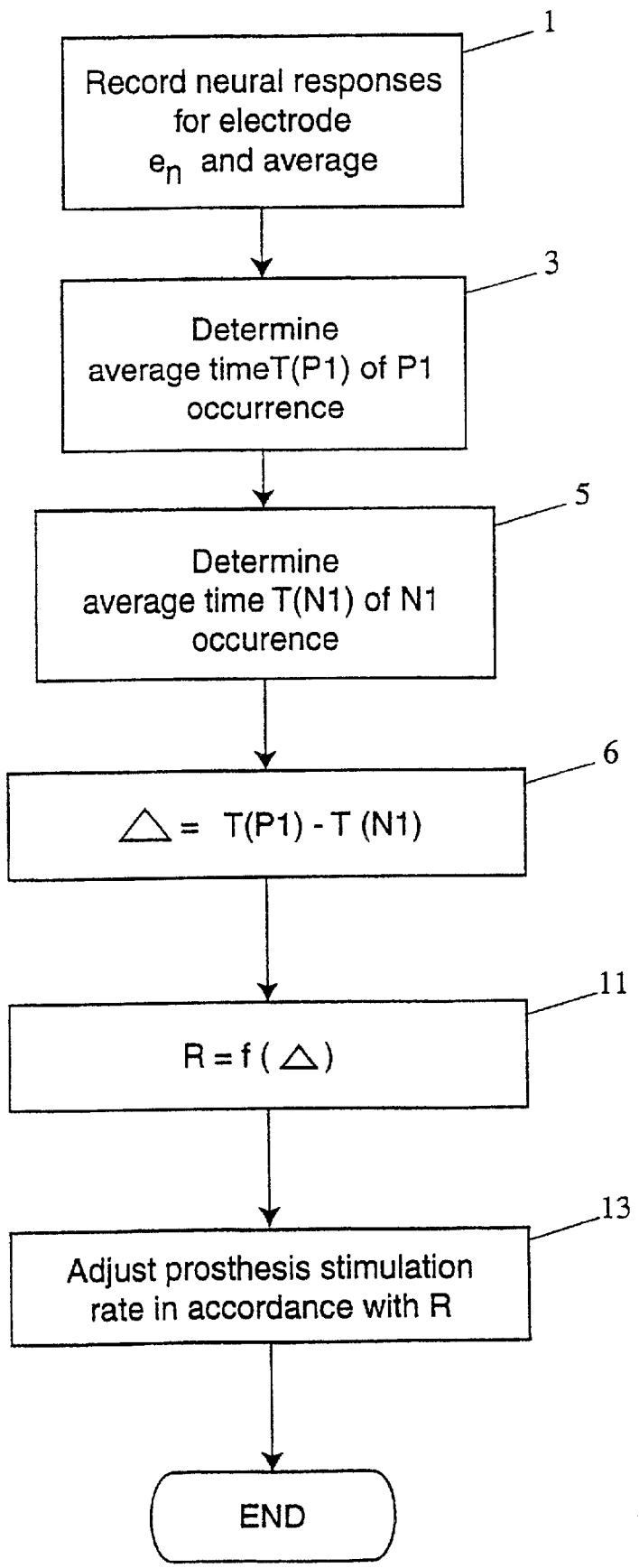
FIG. 2 is a flowchart of a method according to the present invention.

Referring now to FIG. 2 the steps of the method according to the previously described embodiment are specified. Initially the patient's neural response in respect of a selected electrode is recorded. Preferably a number of neural responses are recorded and averaged as shown at box 1. The averaged waveform is then processed to determine the time T(P1) at which the first positive peak, P1, occurs. Methods for making such a determination are well known in the fields of numerical mathematics and computer science and so will not be described in detail here. Similarly at box 5 the time T(N1) at which the first negative peak occurs is determined and stored. At box 6 the difference, Δ, between T(P1) and T(N1) is calculated and stored. While the latency value Δ that has been used in the present example comprises T(P1)–T(N1) as has been previously mentioned other values for latency could be calculated such as T(P1)–T(stim), T(N1)–T(stim) or T(P2)–T(stim) although in each case the aforementioned values of K, c1 and c2 would have to be re-determined. At box 11 the value of Δ calculated in box 6 is used as an argument in the function R=f(Δ) and so an optimal stimulation rate is calculated.

While the above embodiment relates to determining a stimulation rate in respect of only one electrode, in a further embodiment the determination of latency periods is made for all of the electrodes, or at least for a number of electrodes taken over the apical to basal range of positions. The latency differences are then combined, for example by averaging or taking the overall maximum, and processed as explained previously.

Furthermore, it will be appreciated that a rate derived at, for example, electrode N, need not necessarily be applied to electrode N, but may be applied to its neighbouring electrodes and/or all available electrodes. Similarly, if M latencies are measured, they may be used to calculate M or fewer rates, to be distributed among any number of electrodes.

Figure 3:
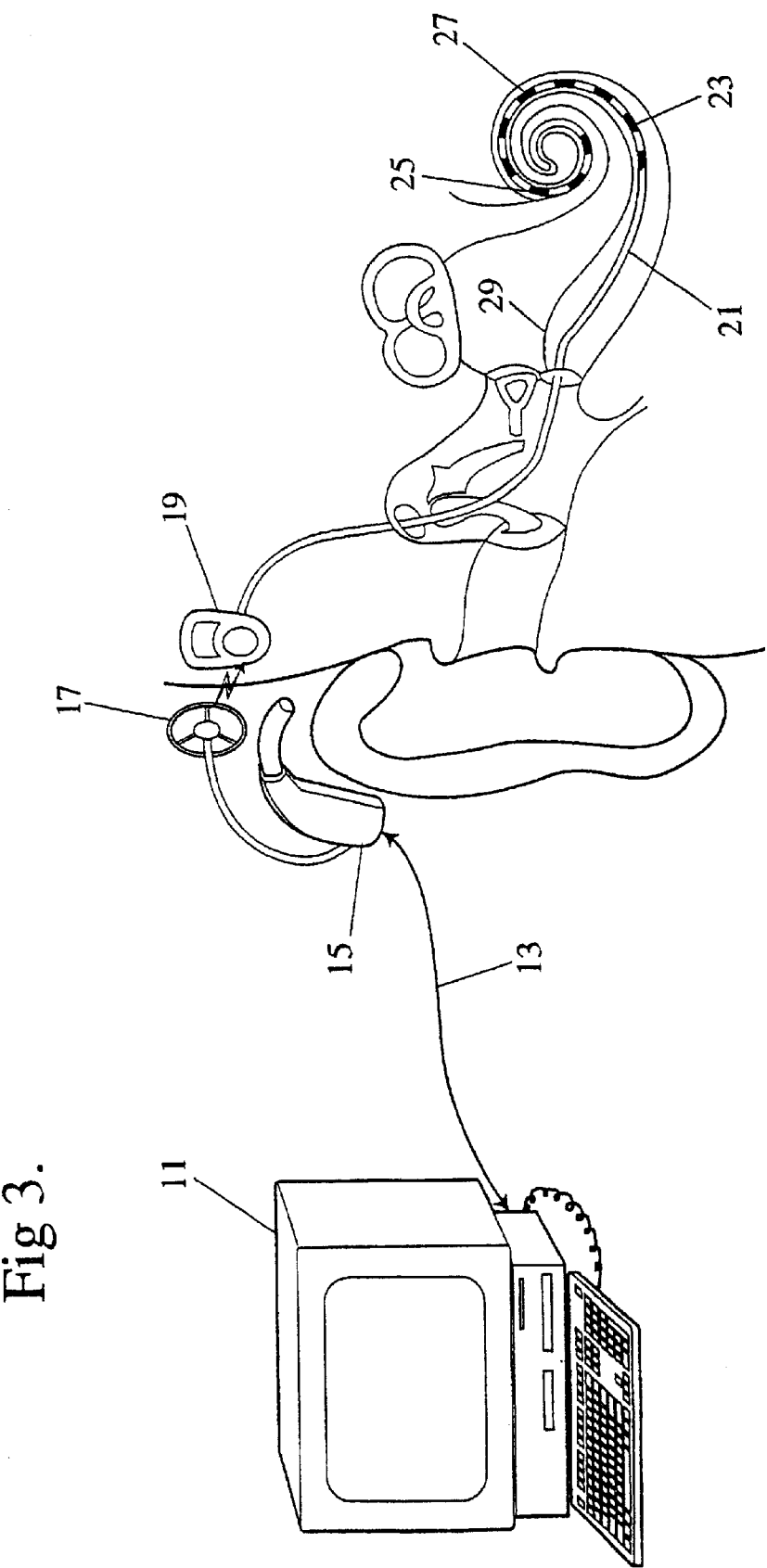
FIG. 3 is a schematic diagram of an apparatus for adjusting or selecting between stimulation strategies of a cochlear implant prosthesis according to the present invention.

Referring now to FIG. 3 there is depicted an apparatus for practising the previously described method. Computer 11 is programmed to carry out the steps illustrated by the flowchart of FIG. 2. The computer is bi-directionally coupled by means of data-link 13 to speech processor 15.

Speech processor 15 is in communication with the implanted portion of the cochlear prosthesis (which includes behind-the-ear processor 15, transmit antenna 17, receiver stimulator 19 and electrode array 21) by means of an inductive link established between transmit antenna 17 and the receive antenna of the receiver stimulator 19. Processor 15 includes non-volatile memory which holds several different speech processing and stimulation strategy programs.

In carrying out the inventive method computer 11 firstly instructs processor 15 to stimulate the auditory system by means of a selected electrode of electrode array 21, electrodes 25, 27 and 23 are identified in FIG. 13. The stimulation command is encoded and transmitted as an RF signal to receiver stimulator 19 where it is decoded and a stimulation current applied by means of the selected electrode. The electrical activity of the auditory system evoked in response to the stimulation, i.e. the neural response, is then detected, encoded and transmitted back to processor 15 by means of the inductive link.

At least one neural response waveform, and preferably several for purposes of averaging, are generated and transmitted from processor 15 to computer 11 by means of link 13.

Computer 11 is programmed to operate upon the received data and to determine an optimal stimulation rate as previously described in reference to FIG. 2. Computer 11 sends a command signal and data signal relating to the optimal data rate to processor 15, which then adjusts its stimulation strategy to accord with the determined optimal rate.

As previously mentioned with reference to FIG. 2, according to a further embodiment latency periods are calculated by computer 11 for a number of electrodes, for example for apical electrode 25, electrode 27 and basal electrode 23. The latency periods are then combined, for example averaged or the largest value selected, and the combined value is compared with a predetermined figure as previously explained. The result of the comparison is then transmitted via link 13 to processor 15. In the event that a high rate stimulation strategy, e.g. ACE is indicated as being beneficial to the patient then processor 15 downloads such a strategy from its non-volatile memory.

It will be further understood by those skilled in the art that the exact demarcation of tasks carried out by computer 11 and by processor 15 does not have to be as explained with reference to the previous embodiment.

For example, in a further embodiment processor 15 incorporates sufficient computational means to execute a program according to the flowchart of FIG. 2, preloaded into internal memory, so that the stimulation rate adjustment can be carried out without recourse to equipment external to the cochlear prosthesis.

While the invention has been explained with reference to a limited number of examples further embodiments and variations are possible and will be apparent to those skilled in the art. Accordingly the following claims are intended to be constructed broadly and not merely restricted to the embodiments described herein.

The claims defining the invention are as follows:

1. A method for adjusting the operation of a cochlear implant prosthesis, said method including the following steps:
   a) recording at least one neural response in respect of at least one electrode of said cochlear implant prosthesis;
   b) determining a selected parameter from said recording;
   c) determining an optimum operation mode for said cochlear implant prosthesis selected on the basis of said selected parameter; and
   d) adjusting the operation of said cochlear implant prosthesis to operatively cause said cochlear implant prosthesis to operative in said optimum operation mode;
   wherein said selected parameter is a latency period; and
   wherein step c) is performed by determining said optimum stimulation rate as a function of said latency period so that $R=(c1/\Delta)+c2$ wherein c1 and c2 are constants, R is the optimum stimulation rate and $\Delta$ is said latency period.

2. A method according to claim 1, wherein said optimum operation mode includes optimising anyone or more of strategy selection, number of channels used, electrode selection, pulse rate, stagger order and conditioner tuning.

3. A method according to claim 1, wherein said latency period is the time from the occurrence of a first identifiable feature of said neural response to the occurrence of a second identifiable feature of said neural response.

4. A method according to claim 3, wherein said first identifiable feature is a first negative peak and said second identifiable feature is a first positive peak of said neural response.

5. A method according to claim 1, wherein said latency period is the time from the application of a stimulation to elicit said neural response to the occurrence of a typical feature of said neural response.

6. A method according to claim 5, wherein said typical feature is the first negative peak of said neural response.

7. A method according to claim 5, wherein said typical feature is the first positive peak of said neural response.

8. A method according to claim 5, wherein said typical feature is the second positive peak of said neural response.

9. A method for adjusting the operation of a cochlear prosthesis including the steps of:
   a) recording neural responses in relation to a plurality of electrodes of said cochlear implant prosthesis;
   b) determining a corresponding plurality of selected parameters from said neural responses;
   c) calculating a combined selected parameter from at least some of said plurality of selected parameters;
   d) determining an optimum stimulation rate on the basis of said combined selected parameters; and
   e) adjusting the operation of said cochlear implant prosthesis thereby causing said prosthesis to operatively apply stimulations to at least some of said plurality of electrodes, all of said plurality of electrodes, and/or any other available electrodes, at a rate dependent on said optimum stimulation rate.

10. A method according to claim 9, wherein said plurality of predetermined parameters is a plurality of latency periods.

11. A system for adjusting the operation of a cochlear prosthesis, said cochlear prosthesis including a means for evoking neural responses of the auditory system to applied stimulation, said system including:
   processing means coupled to said cochlear prosthesis and arranged to analyse said neural responses in order to determine an optimal performance mode dependent on at least one selected parameter derived from said neural responses and to cause said cochlear prosthesis to operate in said optimal mode;
   wherein said selected parameter is a latency period;
   wherein optimal performane is determined by determining said optimum stimulation rate as a function of said latency period so that $R=(c1/\Delta)+c2$ wherein c1 and c2 are constants, R is the optimum stimulation rate and $\Delta$ is said latency period.

12. A system according to claim 11, wherein said processing means is integral with said cochlear prosthesis.

13. A system according to claim 11, wherein said optimum operation mode includes optimising anyone or more of strategy selection number of channels used, electrode selection, pulse rate, stagger order and conditioner tuning.

14. A method for adjusting the operation of a cochlear implant prosthesis, said method including the following steps:
   a) recording at least one neural response in respect of at least one electrode of said cochlear implant prosthesis;
   b) determining a selected parameter from said recording;
   c) determining an optimum operation mode for said cochlear implant prothesis selected on the basis of said selected parameter; and
   d) adjusting the operation of said cochlear implant prosthesis to operatively cause said cochlear implant prosthesis to operative in said optimum operation mode;
   wherein said selected parameter is a latency period;
   wherein step c) is performed by determining said optimum stimulation rate R as a function of said latency period $\Delta$ so that if $\Delta<K$ then $R=A$, else $R=B$; where $A>B$ and K is a predetermined constant.

15. A system for adjusting the operation of a cochlear prosthesis, said cochlear prosthesis including a means for evoking neural responses of the auditory system to applied stimulation, said system including:
   processing means coupled to said cochlear prosthesis and arranged to analyse said neural responses in order to determine an optimal performance mode dependent on at least one selected parameter derived from said neural responses and to cause said cochlear prosthesis to operate in said optimal mode;
   wherein said selected parameter is a latency period;
   wherein optimal performance is determined by determining an optimum stimulation rate R as a function of said latency period so that if $\Delta<K$ then $R=A$, else $R=B$; where $A>B$ and K is a predetermined constant.

* * * * *